(12) United States Patent
Fair et al.

(10) Patent No.: US 7,428,842 B2
(45) Date of Patent: Sep. 30, 2008

(54) PHASED ARRAY ULTRASONIC TESTING SYSTEM AND METHODS OF EXAMINATION AND MODELING EMPLOYING THE SAME

(75) Inventors: Michael Fair, Oakmont, PA (US); Waheed A. Abbasi, Murrysville, PA (US); Michael J. Metala, Murrysville, PA (US); Walter Matulewicz, New Kensington, PA (US)

(73) Assignee: Siemens Power Generation, Inc., Orlando, FL (US)

( * ) Notice: Subject to any disclaimer, the term of this patent is extended or adjusted under 35 U.S.C. 154(b) by 389 days.

(21) Appl. No.: 11/157,050

(22) Filed: Jun. 20, 2005

(65) Prior Publication Data

US 2006/0283250 A1 Dec. 21, 2006

(51) Int. Cl.
*G01N 29/26* (2006.01)
*G01N 29/24* (2006.01)
*G01N 29/06* (2006.01)

(52) U.S. Cl. ............................. 73/626; 73/625; 73/628; 73/602

(58) Field of Classification Search .................. 73/660, 73/593
See application file for complete search history.

(56) References Cited

U.S. PATENT DOCUMENTS

| | | | |
|---|---|---|---|
| 4,497,210 A | | 2/1985 | Uchida et al. |
| 4,821,575 A | * | 4/1989 | Fujikake et al. ............... 73/626 |
| 5,408,884 A | | 4/1995 | Sabourin |
| 6,082,198 A | | 7/2000 | Sabourin et al. |
| 6,202,489 B1 | | 3/2001 | Beffy et al. |
| 6,279,397 B1 | | 8/2001 | Dwyer |
| 6,382,028 B1 | * | 5/2002 | Wooh et al. .................... 73/602 |
| 6,543,272 B1 | | 4/2003 | Vitek |
| 6,725,722 B1 | | 4/2004 | Murphy et al. |
| 6,736,011 B2 | | 5/2004 | Zayicek et al. |

(Continued)

FOREIGN PATENT DOCUMENTS

| | | | |
|---|---|---|---|
| JP | 61198056 A | * | 9/1986 |
| JP | 2005121660 A | * | 5/2005 |
| KR | 2005019518 A | * | 3/2005 |

OTHER PUBLICATIONS

Sabourin, "Field Application for Ultrasonic Linear Phased Array Inspection of Straddle-Mount and Axial-Entry Disk Blade Attachments," Dec. 2000, pp. 1-2.
Moles, "Introduction to Phased Array Ultrasonic Technology Applications: R/D Tech Guideline," 2004, pp. 1-12, R/D Tech Inc.
Siemens Westinghouse, "Challenges Inspecting Siemens Westinghouse Disc Bores," pp. 1-4.

*Primary Examiner*—Hezron E. Williams
*Assistant Examiner*—Rose M Miller

(57) ABSTRACT

A phased array ultrasonic testing system is for examining turbine disc bores and blade attachments for discontinuities, such as stress corrosion cracking. The system is particularly suited to perform an accurate and efficient inspection of components despite their having a relatively complex geometry, such as axial entry blade attachments and bores of associated discs. The system includes a control system with a computer and a controller for programming, emitting, and steering an ultrasonic beam via at least one two-dimensional phased array probe, thereby precisely inspecting the area of interest while simultaneously accommodating the aforementioned complex geometry of the disc or blade attachment. Computer control of the beam permits the number of inspection locations and the number of different probe wedges to be reduced providing for an efficient, timely inspection. Methods of profiling and examining turbine components of known and unknown geometries, are also disclosed.

24 Claims, 6 Drawing Sheets

U.S. PATENT DOCUMENTS

| | | |
|---|---|---|
| 6,789,427 B2 | 9/2004 | Batzinger et al. |
| 6,792,809 B1 | 9/2004 | Moore |
| 6,886,407 B1 * | 5/2005 | Fredenberg .................. 73/622 |
| 7,010,982 B2 * | 3/2006 | Bergman ..................... 73/618 |
| 7,017,414 B2 * | 3/2006 | Falsetti et al. ................ 73/600 |
| 7,174,788 B2 * | 2/2007 | Czerw et al. .................. 73/620 |
| 2002/0088282 A1 * | 7/2002 | Zayicek et al. ................ 73/628 |
| 2004/0016299 A1 * | 1/2004 | Glascock et al. .............. 73/638 |
| 2006/0065055 A1 * | 3/2006 | Barshinger et al. ............ 73/609 |
| 2007/0000328 A1 * | 1/2007 | Buttram ....................... 73/597 |

* cited by examiner

PHASED ARRAY ULTRASONIC TESTING SYSTEM AND METHODS OF EXAMINATION AND MODELING EMPLOYING THE SAME

BACKGROUND OF THE INVENTION

1. Field of the Invention

The present invention relates generally to ultrasonic non-destructive testing and, more particularly, to a phased array ultrasonic testing system for inspecting turbine blade attachments and disc bores. The invention also relates to methods of examining turbine blades and disc bores, and modeling turbine components of unknown geometry using a phased array ultrasonic testing system.

2. Background Information

Gas and steam turbines for electrical power generation must be routinely inspected in order to detect discontinuities, such as stress corrosion cracking (SCC). SCC can result from the combination of high operational forces and prolonged exposure to a corrosive environment. Two portions of the turbine which are areas of relative stress concentration and, therefore, are especially susceptible to SCC, are the blade attachments, where the base or root of the turbine blades attach to the turbine disc, and the bore of the turbine disc. Defects in these and other areas must be identified before they progress to a point where they could result in component failure.

Non-destructive evaluation (NDE) methods, such as ultrasonic testing (UT), are typically employed to inspect turbine blade attachments and disc bores. Ultrasonic testing is generally old and well known in the art. In general, high frequency sound waves are applied to the structure being tested using one or more transducers. The transducers typically comprise piezocrystal elements that are excited by an electrical voltage in order to induce the ultrasonic waves in the structure. When the sound waves interact with something (e.g., a void; a crack or other defect) having a significant difference in impedance from that of the propagation medium, a portion of the sound is either reflected or diffracted back to the source from which it originated. Detection and quantification of the returned sound pattern is used to determine the characteristics of the reflecting medium. The concepts of ultrasonic testing and, in particular, phased array ultrasonic technology, are explained in further detail in the book *Introduction to Phased Array Ultrasonic Technology Applications*, by Dr. Michael D. C. Moles et al., R&D Tech Inc., 2004.

Phased array ultrasonic technology generally provides for the computer-controlled excitation (e.g., amplitude and delay) of individual elements in a multi-element probe (as opposed to single-element probes of conventional UT). The excitation of piezocomposite elements can generate a focused ultrasonic beam with the potential to modify beam parameters such as angle, focal distance, and focal point, through software. Thus, a computer-controlled beam scanning pattern can be implemented in order to "steer" (e.g., direct) the beam to the area of interest and to search for cracks or other discontinuities.

FIG. 1 is a cross-sectional simplified view of a representative example of a turbine rotor assembly 1. The rotor assembly 1 generally includes a shaft 3 having a plurality of discs 5 mounted coaxially thereon. The shaft 3 extends through the bore formed at the center of each disc 5. A plurality of blades 7 are mounted to the periphery of each disc 5. In the example of FIG. 1 the blades 7 are mounted by insertion of a root portion 9 of the blade 7 formed along the circumference of the disc 5. This area is generally referred to as the blade attachment 9. As previously discussed, both the bores of the discs 5 and the blade attachments 9 must be routinely inspected.

Turbine components and, in particular, blade attachment and disc designs and configurations can differ significantly among the various manufacturers in the power generation field. By way of example, most, if not all, turbine blades are attached to the discs using one of two known blade attachment configurations, a side-entry (e.g., generally perpendicular to the shaft axis) configuration commonly referred to as a straddle-mount configuration, or an axial configuration wherein the blades attach to the disc in a direction which is generally parallel to the axis of the shaft. Axial blade attachments and associated discs have much more complicated geometries than their straddle-mount counterparts. Specifically, unlike axial configurations in which the blade attachments and the discs in general have a number of compound curves including curved, contoured, and otherwise irregular geometries, straddle-mount attachments have a relatively simple geometry substantially devoid of compound curvature, for example, and instead consist of a series of substantially straight mounting (grooves. The associated straddle-mount discs are also relatively simple in shape. For example, the sides of the disc are generally straight or flat between the blade attachment area and the disc bore. Straddle-mount blade attachments and discs therefore, are available from the General Electric Company which has a place of business in Niskayuna, N.Y. The axial entry design is available from Siemens Westinghouse Power Corporation which has a place of business in Orlando, Fla.

Inspection using ultrasonic testing techniques gets more and more difficult as the complexity of the geometry of the object to be tested increases. For instance, compound curves make ultrasonic testing very difficult because one portion of the compound curve may, for example, be convex and therefore function to diverge the ultrasonic wave being projected by the transducer while another portion may, for example, be concave and therefore tend to converge the beam. Both the axial mount blade attachments and the sides of the associated discs, for example, have at least one compound curve. As a result of the complexity of the design, commercially available ultrasonic inspection has been limited. NDE has, therefore, been largely limited to surface sensitive techniques such as magnetic particle, dye penetrant, or eddy current. Accordingly, it is appreciated that examining Siemens Westinghouse discs and blade attachments is more difficult than examining discs and blade attachments of other manufacturers. Some of the additional difficulties associated with inspection of Siemens Westinghouse disc bores are outlined in the paper entitled "*SWPC Disc Bore Inspection Method: Challenges Inspecting Siemens Westinghouse Disc Bores*," Siemens Westinghouse.

Although there have been many attempts to apply various ultrasonic testing techniques to the inspection of turbine components, there remains a very real and substantial need for an improved ultrasonic testing system capable of accommodating the complex geometry of for example, axial entry turbine blade attachments and turbine discs.

For example, with respect to inspection of blade attachments, U.S. Pat. No. 6,082,198, discloses a method of using phased array ultrasonic sensors mounted on one of the turbine disc hubs in order to inspect the opposite face. The method is intended to simultaneously reconstruct and test straddle-mount turbine hubs with the turbine blades in place. However, the method is limited in application to the relatively simple geometry of the straddle-mount design, as previously discussed. The disclosed probe mounting location and scanning methods would not sufficiently accommodate the complex geometry of, for example, the axial blade attachment design to provide accurate and reliable inspection results.

With respect to ultrasonic inspection of turbine discs, U.S. Pat. No. 6,736,011, for example, discloses a linear ultrasonic array probe for detecting and inspecting for SCC in the area of the disc bore and keyway of shrunk-on steam turbine discs. However, the method is generally limited to linear or one-dimensional inspection probes and methods, and to the requirement that the probes be placed on the disc at a location across from the keyway area.

There is, therefore, room for improvement in systems and methods for ultrasonic examination of turbine blade attachments and disc bores, and in methods of modeling and examining turbine components of unknown geometry.

SUMMARY OF THE INVENTION

These needs and others are satisfied by the present invention, which is directed to a system and method for inspecting industrial machinery, such as turbine components, using advanced phased array ultrasonic testing apparatus and methods capable of accommodating any complex geometry of the components.

As one aspect of the invention, a phased array ultrasonic testing system is provided for examining an industrial machinery component. The component may be a portion of a turbine. The turbine includes a disc having a bore, and a plurality of blades peripherally mounted on the disc by a blade attachment. At least part of the portion of the turbine to be examined may have a complex geometry. The phased array ultrasonic testing system comprises: an ultrasonic transducer structured to be coupled to the disc at a first location in order to emit an ultrasonic beam from the first location toward the portion of the turbine which is to be examined; and a control system adapted to define a plurality of focal laws of the ultrasonic beam, control the emission of the beam from the ultrasonic transducer, and to steer and focus the beam in order to conduct a non-destructive examination of the portion of the turbine to be examined while accommodating the complex geometry of the at least a part thereof.

The control system may comprise a computer and a controller wherein the computer is structured to program the controller which is adapted to manipulate the transducer in order to perform the examination. At least one of the transducers may be a two-dimensional phased array probe having a plurality of elements wherein the control system is adapted to actuate the elements in order to steer the beam in a first direction and in a second direction to accommodate the complex geometry of the portion of the turbine to be examined. The complex geometry of the portion of the turbine to be examined may comprise at least one compound curve.

The portion of the turbine to be examined may be the bore of the disc. It may also be the blade attachment where the blades mount to the disc.

The ultrasonic transducer may include a plurality of probes wherein at least one of the probes is structured to be mounted on the blade and to be controlled by the control system in order to acquire profiling data to profile the geometry of the portion, when the geometry is unknown. Another of the probes may be mounted on the disc in order to acquire additional profiling data.

As another aspect of the invention, a method of ultrasonically examining a portion of a turbine comprises the steps of: coupling an ultrasonic transducer to a first location on the turbine; calculating a plurality of focal laws for an ultrasonic beam which is to be emitted from the transducer in order to examine the portion of the turbine; programming a control system in accordance with the focal laws in order to control the emission of the beam from the transducer; and steering and focusing the beam to the portion of the turbine to be examined while adjusting for any complex and irregular geometry of the turbine.

The method may further comprise collecting ultrasonic data from the portion of the turbine and analyzing the data in order to detect discontinuities therein. The method may further comprise examining as the portion of the turbine a disc bore and/or a blade attachment.

The method may still further comprise modeling the geometry of the portion of the turbine when the geometry is unknown wherein modeling the geometry comprises: employing a plurality of probes to acquire profiling data of the portion of the turbine; and analyzing the data in order to profile the geometry of the portion. The modeling step may further comprise: coupling at least one of the probes to a blade of the turbine in order to acquire profiling data from the blade; and coupling another of the probes to a disc of the turbine in order to acquire additional profiling data from the disc.

Performing the ultrasonic examination of the portion of the turbine may involve using an ultrasonic testing technique selected from the group consisting of pulse echo, pitch catch, electronic scanning, dynamic depth focusing, sectorial scanning, and a combination of pulse echo, pitch catch, electronic scanning, dynamic depth focusing, and sectorial scanning.

The method may further comprise programming a controller of the control system using a computer, including defining the focal laws for the ultrasonic beam. The programming step may comprise defining as the focal laws, focal laws selected from the group consisting of beam angle, focal distance, beam width, and focal point.

BRIEF DESCRIPTION OF THE DRAWINGS

A full understanding of the invention can be gained from the following description of the preferred embodiments when read in conjunction with the accompanying drawings in which.

DESCRIPTION OF THE PREFERRED EMBODIMENTS

Figure 1:
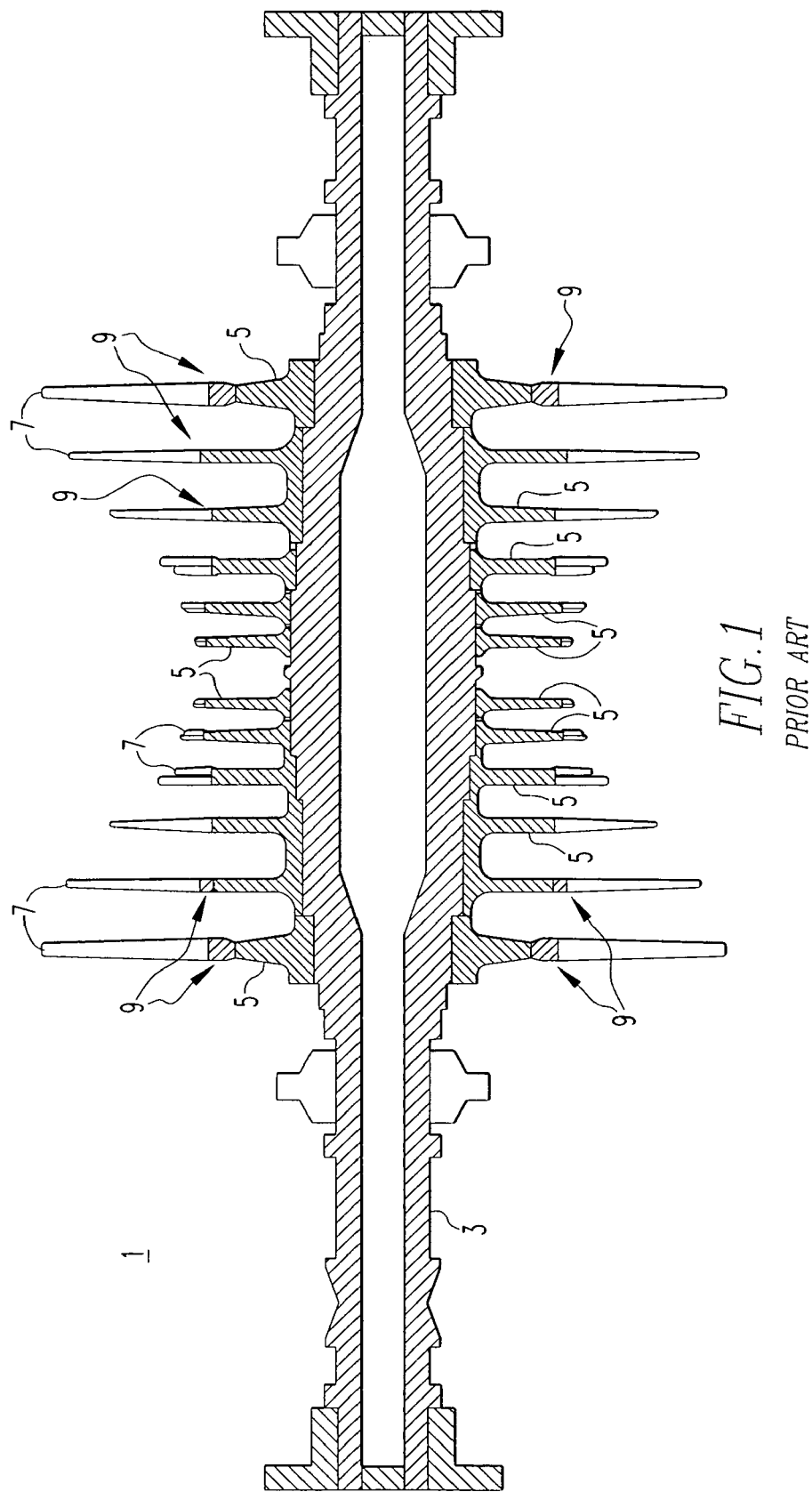
FIG. 1 is a cross-sectional view of a prior art turbine rotor assembly.

The invention will be described as applied to the ultrasonic inspection of power generation turbines (e.g., combustion turbines; steam turbines), although it will become apparent that it could also be applied to ultrasonically inspect a wide variety of other power generation equipment (e.g., without limitation, electrical generators and other components at power plants and other utility sites), and other industrial equipment, generally.

Directional phrases used herein, such as, for example, upper, lower, top, bottom, left, right, and derivatives thereof, relate to the orientation of the elements shown in the drawings and are not limiting upon the claims unless expressly recited therein.

As employed herein, the statement that two or more parts are "coupled" together shall mean that the parts are joined together either directly or joined through one or more intermediate parts.

As employed herein, the term "number" shall refer to one and more than one (i.e., a plurality).

As employed herein, the phrase "complex geometry" refers to an object that has a variety of different shapes and configurations, such that one portion of the object has a shape or configuration which is substantially different from another portion of the object. For example, without limitation, a compound curve is a complex geometry as used herein. A compound curve is one that changes or varies in more than one direction or dimension (e.g., includes both convex and concave portions).

Figure 2:
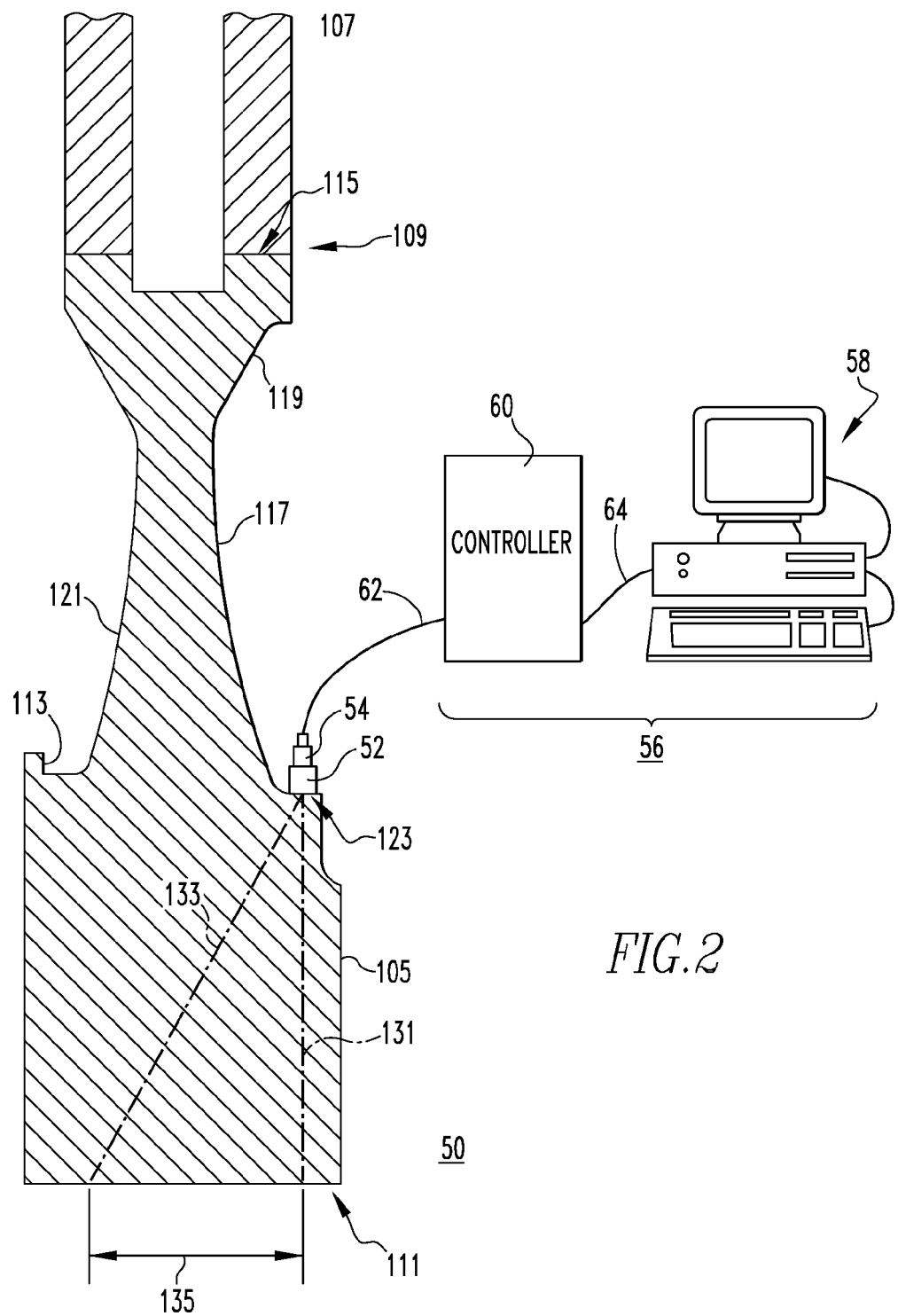
FIG. 2 is a simplified view of a phased array ultrasonic testing system as employed to inspect the bore of a turbine disc in accordance with the invention, with the disc and a portion of a blade being shown in cross-section.

FIG. 2 shows a phased array ultrasonic testing system 50 in accordance with the invention. In the example of FIG. 2, the system 50 includes at least one ultrasonic transducer or probe 54 (one probe 54 is shown) in communication with a control system 56 adapted to steer an ultrasonic beam 131, 133 emitted from the probe 54. Referring briefly to FIG. 5, it will be understood that the term "steer" refers to the ability to control or direct the ultrasonic beam (e.g., beams 131, 133 of FIG. 2). In this manner, as will be discussed in further detail herein, the invention provides for an efficient system 50 an method wherein a relatively large section 135 (FIG. 2) of an object, such as the turbine disc 105 of FIG. 2, can be inspected from a single probe mounting area 123, using a single probe 54 and a single wedge 52.

As will be discussed, the beam parameters are controlled by control system 56. The exemplary control system 56 includes a computer 58 and a controller 60. The controller 60 can be any known or suitable phased array probe control unit adapted to manipulate the probe 54. More specifically, the computer 58 contains software for programming the controller 60 to manipulate the probe 54 in accordance with a predetermined set of focal laws. Accordingly, in operation, beam parameters such as, for example, angle, focal distance, and focal point, which collectively form the focal laws of the probe 54, can be entered and modified using the computer 58 in order to program the controller 60 to control the probe 54 in order to perform an examination of the desired portion of the turbine, in accordance with such focal laws. By way of a non-limiting example, one known phased array probe controller is commercially available under the trade designation TomoScan III, which is available from R/D Tech of Quebec, Canada. It will be appreciated that additional systems (not shown) could be employed in combination with the phase array probe control unit 60 of the invention. For example, without limitation, a motion control unit may be used to control a delivery mechanism, for example, for automatically positioning and installing the probes.

FIG. 2 shows an ultrasonic test being performed to inspect the bore 111 of the turbine disc 105. The blade attachment 109 and portion of the blade 107 is also shown and is inspected in a similar manner. The disc 105 and blade 107 shown in the example of FIG. 2 are of the axial mount design. As previously described, the components of such design have a relatively complex geometry (best shown in FIG. 3). The phased array ultrasonic testing system 50 (FIG. 2) and computer-controlled examination methods of the invention are capable of accommodating this complex geometry while simultaneously conducting an accurate non-destructive examination of the desired turbine portion. More specifically, Siemens Westinghouse discs 105 of the type shown in simplified form in the examples of FIGS. 2 and 3, have a number of compound curves making for a relatively complex geometry, as previously discussed. In particular, the sides of the disc 105 between the axial blade attachment 109 and the bore 111 have at least first, second and third sloped areas 117, 119, 121, respectively, each of which has a different slope and/or radius or radii of curvature, as shown. The disc 105 also includes a variety of other relatively complex features, such as the lifting ring groove 113 and steeple 115, which can vary from disc to disc and from front to back (from the perspective of FIG. 2). For example, without limitation, the steeples 115 may be curved (not shown), and/or they may also be tapered, for example, so as to have a larger dimension at the front (from the perspective of FIG. 2) and taper to a smaller dimension at the back (from the perspective of FIG. 2)(not shown). Furthermore, it is also not uncommon within the scope of such turbine design to stack more than one blade row on a single disc 105. All of these relatively complex features add to the difficulty in accurately ultrasonically examining the blade attachments 109 and disc bores 111 of the turbine.

A further understanding of the invention may be had by describing the exemplary system and methods as applied to inspect the disc bore 111.

As previously discussed, known disc bore ultrasonic testing techniques have generally been limited to linear or one-dimensional (1D) probes and methods of the type described, for example, in U.S. Pat. No. 6,736,011. The probe 54 and phased array ultrasonic testing system 50 of the invention provide for two-dimensional (2D) inspection which, as will now be described, is much more efficient and suitable for accommodating complex geometries.

Specifically, as shown in FIG. 2, the probe, whether it is a conventional 1D (not shown) or a 2D probe 54 (best shown in FIG. 5), is mounted on a wedge 52 at the probe mounting location 123 on the disc 105. From this location, the beam 131 is emitted from the probe 54 through the wedge 52 and then through the object being tested (e.g., disc 105). Thus, the wedge 52 serves as an optical lens-type device in order to further control (e.g., direct; steer) the beam to the desired examination area (e.g., bore 111). In this manner, the wedge 52 can partially control, for example, without limitation, the width and direction of the beam 131 to "focus" on the area of interest. However, the steering capabilities of a particular wedge 52 are limited. Accordingly, it will be appreciated that known 1D probes required multiple wedges in order to inspect, for example, an area of the bore 111, such as area 135 in FIG. 2. Selection, placement and replacement of multiple wedges on the test article is a time-consuming process which greatly adds to the overall duration of the inspection. Although advancements have been made in the art to try and make wedge 52 and sensor or probe 54 placement more efficient (see, e.g., "Self-aligning Turbine Disc Inspection Apparatus" disclosed in U.S. Pat. No. 6,792,809), it is desirable to reduce the number of wedges needed to accurately perform the inspection. The phased array ultrasonic testing system 50 and methods of the invention successfully achieve this goal by providing 2D beam steering capabilities and advanced computer programming and control of the probe 54.

To further illustrate this improved aspect of the invention, with continued reference to FIG. 2, a non-limiting EXAMPLE comparing known ultrasonic probes and testing methods and the exemplary system 50 and method will now be provided. The following EXAMPLE is merely provided for illustrative purposes and is in no way limiting upon the scope of the present invention.

EXAMPLE

Figure 3:
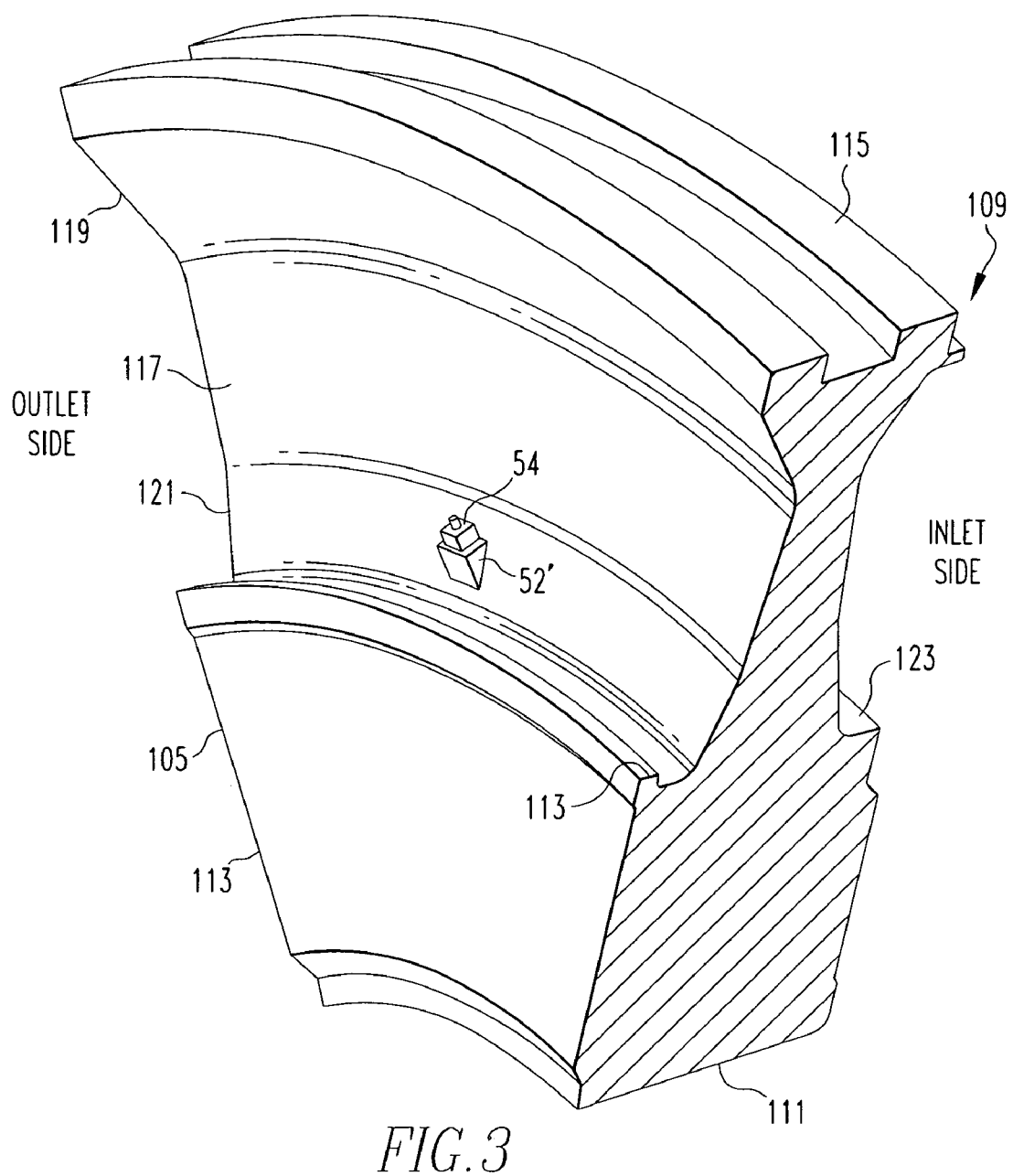
FIG. 3 is an isometric view of a portion of the disc of FIG. 2 and a two-dimensional phased array probe mounted on the outlet side of the disc.

For this example, the area of the disc bore 111 to be examined is designated by the dimension 135, which is about 2 inches (5.08 centimeters) wide. In order to inspect area 135 using known ultrasonic testing techniques would require about six different wedges (not shown), whereas the same area 135 can be inspected using a single wedge 52 in accordance with the exemplary phased array ultrasonic testing system 50. This is, in large part, due to the fact that known 1D techniques are limited in their ability to steer the beam 131 over a relatively large area. Specifically, as previously discussed, one-dimensional probes can only steer in one direction which makes it difficult to control the beam as desired when the wedge and probe are mounted on a surface that is not flat. The various probe mounting surfaces on disc 105 (two different mounting surfaces are shown in FIGS. 2 and 3, respectively), are not flat. Therefore, the aforementioned plurality (e.g., six) of different wedges would be required to accommodate the irregular geometry of the disc 105 by diverging, converging or otherwise focusing, for example, the beam to the desired examination area.

Conversely, probe 54 of the invention is programmable and controllable (e.g., can be focused) in two dimensions. Focusing the probe 54 through the exemplary control system 56 and, in particular, by programming the controller 60 with the desired focal laws rather than by interchanging a plurality of different wedges to achieve a similar result, substantially streamlines the inspection process. Specifically, whereas a conventional disc bore inspection would take about 36 hours or three 12-hour shifts, the exemplary system 50 and method are expected to substantially reduce the duration of such an inspection. Specifically, it is anticipated that the system 50 could potentially reduce inspection time to about one 12-hour shift which would result in a turbine down time of potentially as little as one day, rather than three. It is also expected that the number of wedges (e.g., 54) required for a typical disc 105 inspection will be reduced by between about 50-80%, or more. This is evidenced in the foregoing EXAMPLE which demonstrates a present reduction in the number of wedges of over 80% from six wedges to a single wedge 52.

FIG. 3 provides an isometric view of a portion of the disc 105 and further illustrates the relatively complex geometry thereof. FIG. 3 also shows another probe mounting location on surface 121 on the outlet side of the disc 105, for emitting an ultrasonic beam (not shown) in order to inspect another section of the disc bore 111. As shown, a different wedge 52' is required in order to couple or mount the probe 54 on the irregular surface 121. It will be appreciated that a wide variety of different probe mounting locations and wedges therefor, other than those shown and described herein, could be employed.

Figure 4:
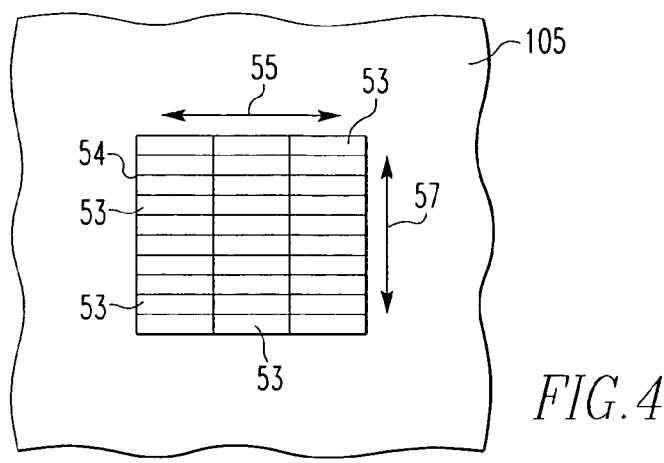
FIG. 4 is a simplified, bottom elevational view of the two-dimensional phased array probe and the elements thereof, of FIG. 3

FIG. 4 is a simplified view of the bottom of the exemplary probe which, as previously discussed, is a 2D phased array probe 54. As shown, the exemplary 2D probe 54 has 30 elements 53 disposed in a 3×10 array. Each element 53 essentially performs as a separate transducer or probe in order to enable the ultrasonic beam 131, 133 (FIG. 2) to be steered in two directions, left to right (from the perspective of FIG. 4) as indicated by arrow 55, and up and down (with respect to FIG. 4) as indicated by arrow 57. Accordingly, as discussed hereinbefore, the single probe 54 can be steered and focused so efficiently that it can effectively perform a comparable inspection using a reduced number of wedges, as compared to 1D designs. It will be appreciated that any known or suitable 2D phased array probe having any suitable number of elements can be employed with the exemplary system 50. A 2D phased array probe of the type illustrated in FIG. 4 is commercially available, for example, without limitation, from Imasonic S.A. which has a place of business in Besancon, France. Generally, phased array probes are custom made in accordance with the requirements of the application in which they will be used. It will also be appreciated that, as will be described herein, the exemplary phased array ultrasonic testing system 50 and methods can also be advantageously employed to improve the performance (e.g., without limitation, steering and focusing capabilities) of 1D phased array probes. The system 50 may also be used to collect data using conventional (e.g., non-phased array probes) sensors (e.g., measurement sensors; thermal sensors; optical sensors) in order to profile turbine components of unknown geometry for subsequent ultrasonic examination thereof It will still further be appreciated that in certain embodiments of the invention, the wedge 52 may be integral to the probe 54 rather than being a separate component to which the probe 54 is attached. For example, the probe 54 may be permanently attached to the wedge 52 at a desired angle.

Figure 5A:
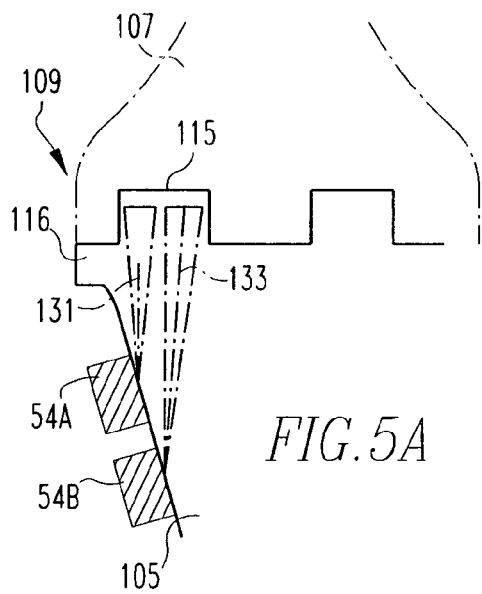
FIG. 5A is a simplified cross-sectional representation of a pulse echo ultrasonic testing method of inspecting turbine disc steeples in accordance with the invention.
Figure 5B:
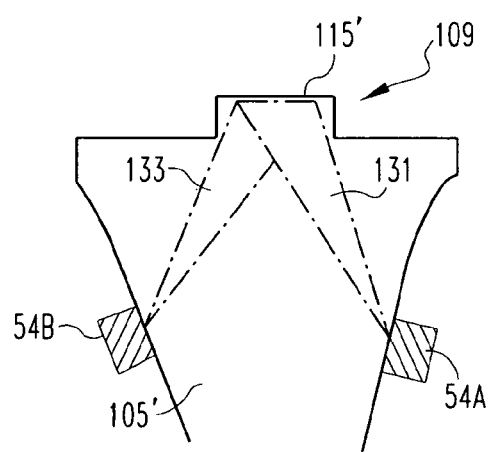
FIG. 5B is a simplified cross-sectional representation of a pitch catch ultrasonic testing method of inspecting turbine disc steeples in accordance with the invention.

It will be appreciated that all of the foregoing also applies with respect to the inspection of blade attachments 109 except that the mounting positions the probes 54 is different. By way of example, FIGS. 5A and 5B show two representative examples of the types or methods of ultrasonic inspection techniques that can be employed using the exemplary system 50 to inspect the blade attachment area 109. For simplicity of disclosure, only a portion of the disc 105, 105' is shown in simplified form and the probes 54A, 54B are shown schematically without a mounting wedge (e.g., wedge 52 of FIG. 2). FIG. 5A shows a pulse echo method used to inspect the steeples of the disc 105, such as steeple 115 which is adjacent tang 116. This area generally comprises the blade attachment area 109 which, in the example of FIGS. 5A and 5B, is an axial entry blade attachment 109. Generally, for pulse echo techniques two or more 2D phased array probes 54A, 54B (two probes 54A, 54B are shown) are positioned generally adjacent one another, as shown. The beam 131, 133 is then emitted from each probe 54A, 54B, respectively, such that when a defect or discontinuity is encountered, the beam 131, 133 bounces back to the probe 54A, 54B, as an echo. The echo is then analyzed using the control system 56 (FIG. 2).

As shown in FIG. 5B, the pitch catch method uses a different probe configuration wherein the first probe 54A is disposed on one side of the test object (e.g., disc 105') and the other probe 54B is disposed on the opposite side. Generally, the pitch catch method involves emitting or pitching a beam 131,133 from one probe 54A, 54B bouncing it off of the desired test area (e.g., steeple 115' of blade attachment 109) and catching it with the other probe 54A, 54B.

The foregoing are merely two examples of the many methods and techniques that can be employed, using the invention, in order to inspect various portions of the turbine. The examples of FIGS. 5A and 5B are not limiting upon the scope of the invention. For example, a wide variety of other known or suitable beam focusing and scanning methods, such as, for example, electronic scanning, dynamic focusing, and/or sectorial scanning (often referred to as azimuthal or angular scanning) can also be employed. Each of these methods are described in detail in *Introduction to Phased Array Ultrasonic Technology Applications*, by Dr. Michael D.C. Moles et al., R/D Tech Inc., 2004.

As previously discussed, the phased array ultrasonic-testing system 50 (FIG. 2) accomplishes the aforementioned advanced ultrasonic testing techniques, despite the complex geometry of the axial entry design, through the computer-controlled manipulation of the probes 54, (FIGS. 2 and 3), 54A, 54B (FIG. 5A and 5B). As shown in FIG. 2, the exemplary probes 54 are coupled to the controller 60 by a first electrical cable 62. The controller 60 is then coupled to the computer 58 by second electrical cable 64, although other configurations (not shown) could be employed without departing from the scope of the invention. For example, a wireless configuration (not shown) could be employed, or the intermediate controller 60, for example, could be eliminated such that the probe 54 is controlled by the computer 58 and software thereof, directly.

It will also be appreciated that any known or suitable software program can be employed to define the focal laws and all of the other necessary parameters for programming the controller 60 to conduct the desired examination. For example, without limitation, one suitable software program is TomoView™, which is commercially available from R/D Tech of Quebec, Canada. TomoView™ is a commercially available software package that can be implemented in control system 56 in order to manage the acquisition of ultrasonic signals and to provide real-time imagining of the signals and/or offline analysis of previously acquired data. This can be used as a stand alone software package for programming the ultrasonic examination to be performed, conducting the examination and acquiring the data, and then analyzing the data for discontinuities. Alternatively, it can be used in conjunction with a wide variety of other known or suitable software packages, which may be used to separately develop the focal laws and to program the controller 60, for example. A more detailed description of the TomoView™ software package and how it can be employed to conduct various ultrasonic examinations can be found, for example, in Chapter 1 of Basic Concepts of Phased Array Ultrasonic Technology, supra.

When a company such as, for example, Siemens Westinghouse examines its own turbine components, parameters regarding the geometry of, for example the blade attachments 109, are known and can merely often be entered into the software when programming the focal laws. For example, engineering drawings or computer models of the components are typically available and can be imported into the software. However, the geometry is not always known such as, for example, when inspecting turbine components manufactured by another company. In such cases, the geometry of the object to be tested must first be modeled or profiled.

Figure 6:
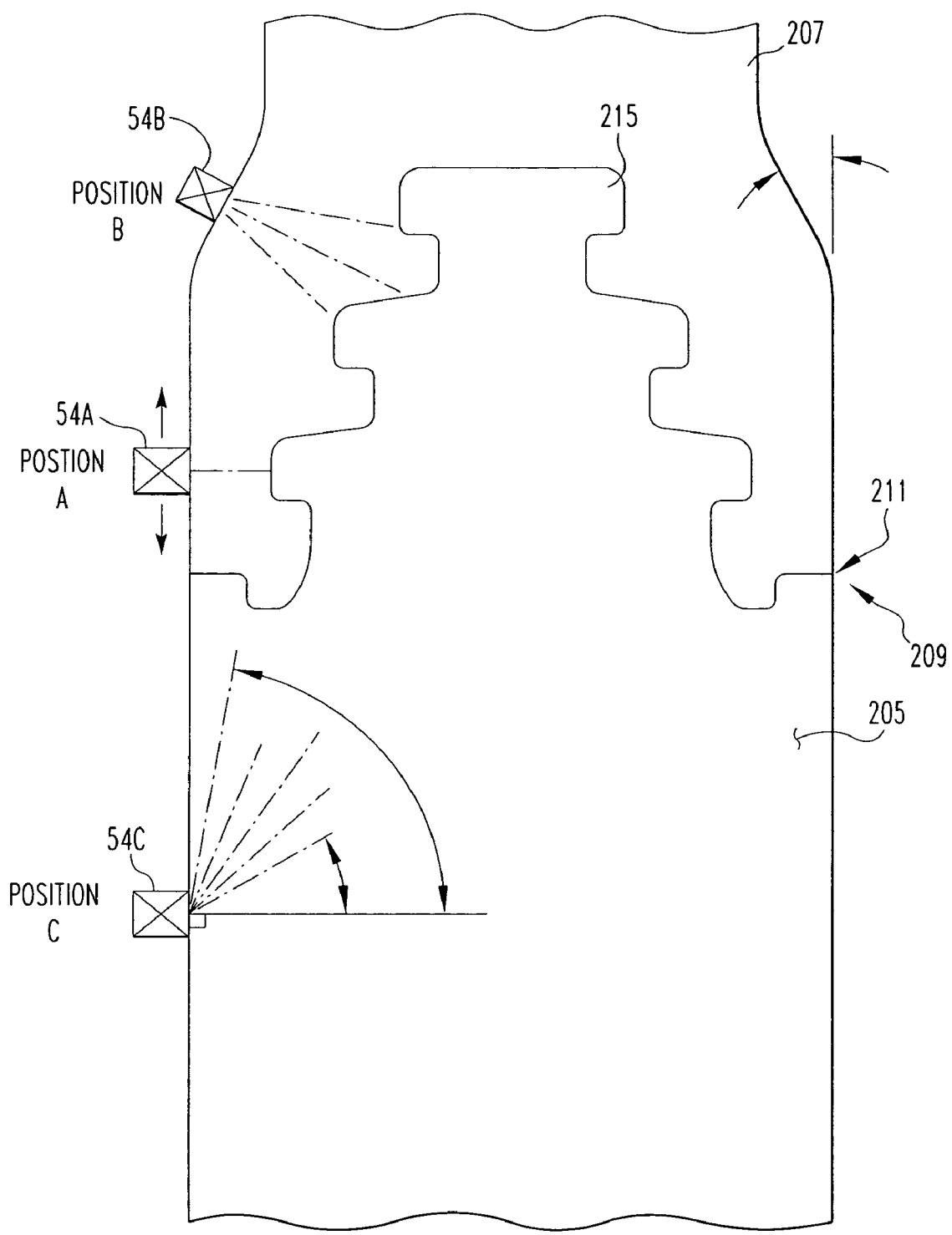
FIG. 6 is a cross-sectional view of a disc, blade, and blade attachment illustrating a method of profiling a blade attachment of unknown geometry using the ultrasonic testing system of the invention.
Figure 7:
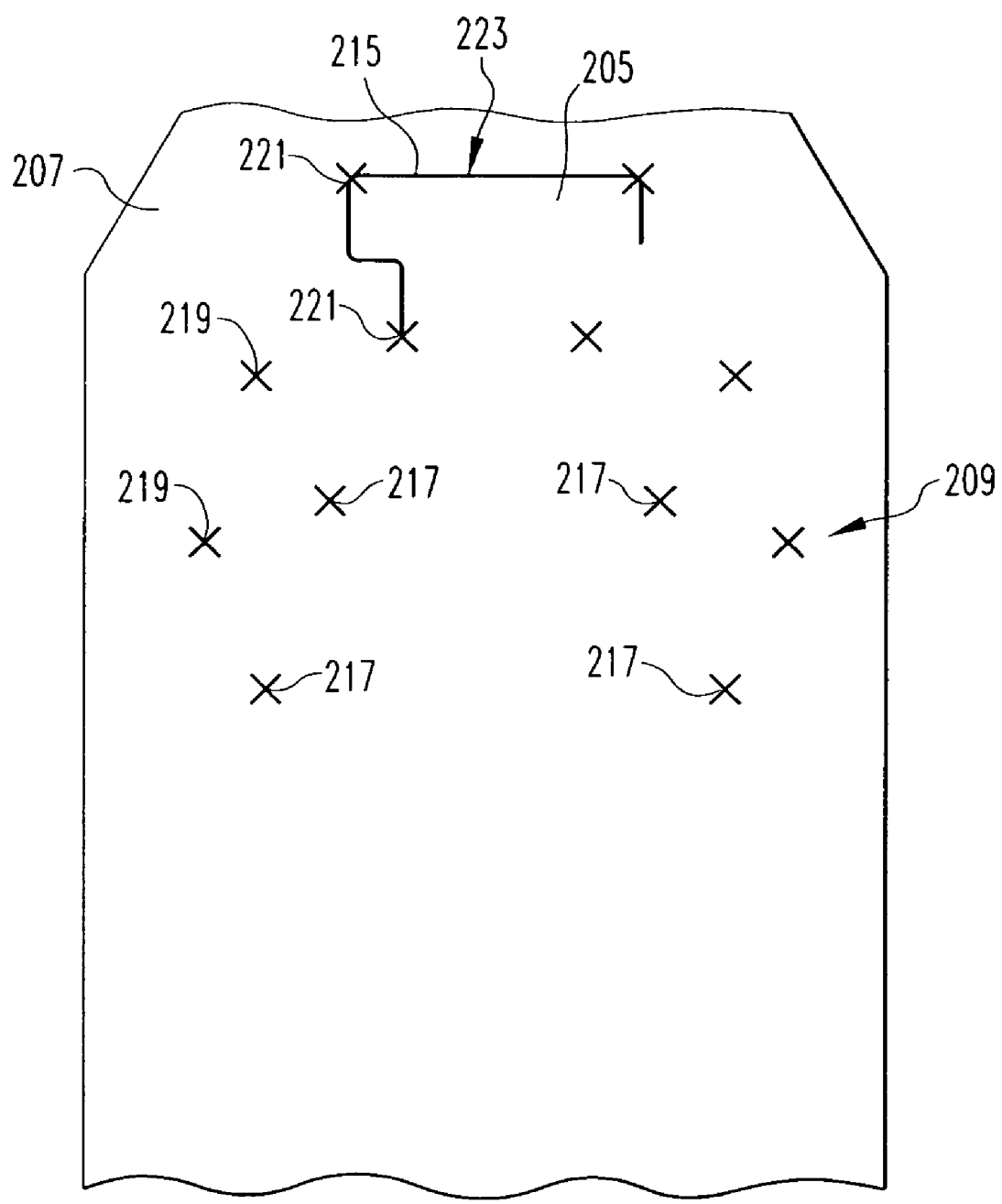
FIG. 7 is a cross-sectional view of the disc, blade and blade attachment of FIG. 6 as the blade attachment is being modeled using profiling data obtained from the ultrasonic testing system of the invention.

As shown in FIGS. 6 and 7, the exemplary testing system 50 may be used to profile turbine components of unknown geometry. For instance, in the example of FIGS. 6 and 7, a blade attachment 209 of generally unknown geometry is being profiled through use of three phased array probes 54A, 54B and 54C. although in other methods contemplated by the invention but not shown, other types and numbers of sensors or probes, at other positions, could be employed. Specifically, assuming that all that is known in the example of FIG. 6 is that the blade attachment 209 is of the straddle-mount variety, the profile and thus the geometry of the blade attachment 209 must be and can be determined using the system 50 of the invention, for example, to measure distance from the sensor to various points on the blade's 207 and disc's 205 surface, in order that it may be subsequently accurately ultrasonically examined for defects.

Unlike the aforementioned reconstruction technique disclosed in U.S. Pat. No. 6,082,198, which is limited to an ultrasonic sector scan from a probe mounted on the hub of the disc, the exemplary profiling method, as illustrated in FIG. 6 uses a number of different probes 54A, 54B, 54C at a number of different locations (see e.g., positions A, B and C), and a combination of different ultrasonic testing techniques. For example, two scans (e.g., azimuthal scans) are shown using probes 54B and 54C at positions B and C on the blade 207 and disc 205, respectively, while a pulse echo technique is being employed at position A. The example of FIG. 6 is not meant to be limiting upon the scope of the invention and it will be appreciated that a wide variety of alternative ultrasonic testing techniques, probe positions, and numbers of probes, could be employed. None-the-less, the example illustrates the key distinctions and advantages of the exemplary geometry modeling method. Namely, a combination of ultrasonic testing methods or techniques is employed as opposed to a limited single scan from a single location. Secondly, unlike the '546 patent, probes 54A, 54B are mounted on the blade 207 in order to collect blade attachment 209 profiling data 219 from the blade 207 as well as from the hub 205, which is a much more accurate and effective method to determine the geometry of the attachment 209, as precisely as possible. Accordingly, because the accuracy of any subsequent ultrasonic examination of the blade attachment 209 depends primarily on the geometry of the blade attachment 209, the invention provides a significant advantage over the known art.

FIG. 7 shows various data 217, 219, 221 collected form the different probes 54A, 54B, 54C of FIG. 6. Data 217 is collected from the scan of the disc 205 using probe 54C, data 219 is from probe 54A on the blade 207, and data 221 is from the scan performed using probe 54B at position B on the blade 207, as shown in FIG. 6. Once collected, the data 217, 219, 221 can be entered in the software, or manually plotted, as previously described, and an accurate profile of the blade attachment 209 can be replicated by essentially connecting the dots between data 217, 219 and 221, as shown by plot line 223 of FIG. 7. After the component (e.g., without limitation blade attachment 209) has been profiled, the exemplary system 50 may be used to program the necessary focal laws and any additional parameters and the component is then ready to be examined. The geometric model in accordance with the aforementioned method of the invention is expected to be of comparable precision to that of a component of entirely known geometry. Thus, any subsequent examination of the component will be accurate and reliable.

Accordingly, the invention provides an advanced system and methods of accurately ultrasonically inspecting components of complex geometry which have heretofore been extremely difficult to examine using conventional ultrasonic testing methods. The invention is further applicable to more efficiently inspect a wide variety of industrial components of known and unknown, complex and simple geometries.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to

What is claimed is:

1. A phased away ultrasonic testing system for examining a portion of an industrial machinery component, at least a part of said portion of said component having a complex geometry, said phased array ultrasonic testing system comprising:
   a phased array ultrasonic transducer structured to be coupled to said component at a first location in order to emit an ultrasonic beam from said first location toward said portion of said component which is to be examined; and
   a control system adapted to define a plurality of focal laws of said ultrasonic beam, control the emission of said beam from said ultrasonic transducer, and to steer and focus said beam in order to conduct a non-destructive examination of the portion of said component to be examined while accommodating the complex geometry of said at least a part thereof,
   wherein an interface is formed at said first location where said phased array ultrasonic transducer is coupled to said component,
   wherein said interface has a complex geometry, and
   wherein said examination is conducted through said complex geometry of said interface.

2. The phased array ultrasonic testing system of claim 1 wherein said control system comprises a computer and a controller; and wherein said computer is structured to program said controller which is adapted to manipulate said transducer in order to perform said examination.

3. The phased array ultrasonic testing system of claim 1 wherein said phased array ultrasonic transducer comprises a two-dimensional phased array probe having a plurality of elements; wherein said two-dimensional phased array probe is mounted in a stationary position on said component; and wherein said control system is adapted to actuate said elements in order to steer said beam in a first direction and in a second direction to accommodate the complex geometry of said at least a part of the portion of said component to be examined.

4. The phased array ultrasonic testing system of claim 1 wherein said industrial machinery component is a portion of a turbine, said turbine including a disc having a bore, and a plurality of blades peripherally mounted on said disc by a blade attachment; and wherein said phased array transducer is structured to be coupled to said disc or at least one of said blades.

5. The phased array ultrasonic testing system of claim 4 wherein said portion of said turbine to be examined is said bore of said disc.

6. The phased array ultrasonic testing system of claim 4 wherein said portion of said turbine to be examined is said blade attachment where said blades mount to said disc.

7. The phased array ultrasonic testing system of claim 4 wherein said complex geometry of said at least a part of said portion of said turbine comprises at least one compound curve.

8. The phased array ultrasonic testing system of claim 4 including a wedge disposed between said disc and said transducer, said wedge structured to couple said transducer to said disc and to further focus said ultrasonic beam on said portion of said turbine being examined.

9. The phased array ultrasonic testing system of claim 4 wherein said ultrasonic transducer includes a plurality of probes; and wherein at least one of said probes is structured to be mounted on one of said plurality of blades and to be controlled by said control system in order to acquire profiling data to profile the geometry of said portion, when the geometry is unknown.

10. The phased array ultrasonic testing system of claim 9 wherein another of said probes is mounted on said disc in order to acquire additional profiling data.

11. The phased array ultrasonic testing system of claim 4 wherein said blade attachments are axial mount blade attachments.

12. A method of ultrasonically examining a portion of an industrial machinery component, the method comprising the steps of:
   coupling an ultrasonic transducer to a first location on said component;
   calculating a plurality of focal laws for an ultrasonic beam which is to be emitted from said transducer in order to examine said portion of said component;
   programming a control system in accordance with said focal laws in order to control the emission of said beam from said transducer;
   steering and focusing said beam to said portion of said component to be examined, while adjusting for any complex and irregular geometry of said component; and
   conducting said examination through an interface formed at said first location where said phased array ultrasonic transducer is coupled to said component, said interface having a complex geometry.

13. The method of claim 12 further comprising collecting ultrasonic data from said portion and analyzing said data in order to detect any discontinuities in said portion.

14. The method of claim 12 further comprising said examined industrial machinery component comprising a turbine.

15. The method of claim 14 further comprising said examined portion of said turbine comprising a disc bore.

16. The method of claim 14 further comprising said examined portion of said turbine comprising a blade attachment.

17. The method of claim 16 further comprising said blade attachment comprising an axial mount blade attachment.

18. The method of claim 14 further comprising modeling the geometry of said portion of said turbine when said geometry is unknown, wherein modeling the geometry comprises:
   employing a plurality of probes to acquire profiling data for said portion of said turbine; and
   analyzing said data in order to profile the geometry of said portion.

19. The method of claim 12 further comprising performing said ultrasonic examination of said portion of said component using an ultrasonic testing technique selected from the group consisting of pulse echo, pitch catch, electronic scanning, dynamic depth focusing, sectorial scanning, and a combination of pulse echo, pitch catch, electronic scanning, dynamic depth focusing, and sectorial scanning.

20. The method of claim 12 further comprising programming a controller of said control system using a computer, wherein said programming includes defining said focal laws for said ultrasonic beam.

21. The method of claim 20 further comprising said focal laws selected from the group consisting of beam angle, focal distance, beam width, and focal point.

22. The method of claim 12 further comprising said phased array ultrasonic transducer comprising a two-dimensional (2D) phased array probe having a plurality of elements; steering said beam in a first direction using said two-dimensional (2D) phased array probe; and steering said beam in a second direction using said two-dimensional (2D) phased array probe.

23. A method of ultrasonically examining a portion of an industrial machinery component, the method comprising the steps of:
- modeling the geometry of said portion of said turbine when said geometry is unknown;
- coupling an ultrasonic transducer to a first location on said component;
- calculating a plurality of focal laws for an ultrasonic beam which is to be emitted from said transducer in order to examine said portion of said component;
- programming a control system in accordance with said focal laws in order to control the emission of said beam from said transducer;
- steering and focusing said beam to said portion of said component to be examined, while adjusting for any complex and irregular geometry of said component;
- wherein said examined industrial machinery component comprises a turbine; and
- wherein modeling the geometry comprises:
  - employing a plurality of probes to acquire profiling data for said portion of said turbine;
  - analyzing said data in order to profile the geometry of said portion;
  - coupling at least one of said probes to a blade of said turbine in order to acquire profiling data from said blade; and
  - coupling another of said probes to a disc of said turbine in order to acquire additional profiling data from said disc.

24. A phased array ultrasonic testing system for examining a portion of an industrial machinery component, at least a part of said portion of said component having a complex geometry, said phased array ultrasonic testing system comprising:
- a phased array ultrasonic transducer structured to be coupled to said component at a first location in order to emit an ultrasonic beam from said first location toward said portion of said component which is to be examined; and
- a control system adapted to define a plurality of focal laws of said ultrasonic beam, control the emission of said beam from said ultrasonic transducer, and to steer and focus said beam in order to conduct a non-destructive examination of the portion of said component to be examined while accommodating the complex geometry of said at least a part thereof,
- wherein said examined industrial machinery component comprises a turbine,
- wherein the geometry of said portion of said turbine is unknown,
- wherein a plurality of probes are coupled to said turbine to acquire profiling data for said portion of said turbine,
- wherein at least one of said probes is coupled to a blade of said turbine in order to acquire profiling data from said blade, and
- wherein another one of said probes is coupled to a disc of said turbine in order to acquire additional profiling data from said disc.

* * * * *